US012766343B2

(12) United States Patent
Heo et al.

(10) Patent No.: US 12,766,343 B2
(45) Date of Patent: Oct. 20, 2026

(54) RADIATION IMAGING DEVICE AND RADIATION IMAGING SYSTEM

(71) Applicant: Vieworks Co., Ltd., Anyang-si (KR)

(72) Inventors: Kang Heo, Seongnam-si (KR); Doo Ho Kim, Anyang-si (KR)

(73) Assignee: Vieworks Co., Ltd., Anyang-si (KR)

( * ) Notice: Subject to any disclaimer, the term of this patent is extended or adjusted under 35 U.S.C. 154(b) by 128 days.

(21) Appl. No.: 18/897,736

(22) Filed: Sep. 26, 2024

(65) Prior Publication Data

US 2025/0099786 A1 Mar. 27, 2025

(30) Foreign Application Priority Data

Sep. 27, 2023 (KR) ........................ 10-2023-0130475

(51) Int. Cl.

*A61N 5/00* (2006.01)
*A61N 5/10* (2006.01)
*G01T 1/24* (2006.01)

(52) U.S. Cl.

CPC .............. *A61N 5/1071* (2013.01); *G01T 1/24* (2013.01); *A61N 2005/1087* (2013.01)

(58) Field of Classification Search

CPC .......... A61N 2005/1087; A61N 5/1071; A61N 2005/1074; A61N 5/1067; G01T 1/24
See application file for complete search history.

(56) References Cited

U.S. PATENT DOCUMENTS 10,690,787 B2 6/2020 Lee
11,684,328 B2 6/2023 Dejongh et al.
2020/0018864 A1 * 1/2020 Lee ......................... H10F 30/29

FOREIGN PATENT DOCUMENTS

KR 2016-0119543 A 10/2016
KR 2020-0008510 A 1/2020
WO 2010-113451 A1 10/2010

* cited by examiner

*Primary Examiner* — Dani Fox
(74) *Attorney, Agent, or Firm* — Bridgeway IP Law Group, PLLC; Jihun Kim

(57) ABSTRACT

Embodiments relate to a radiation imaging device and a radiation imaging system, and more particularly, to a radiation imaging device and a radiation imaging system capable of monitoring, in real time, a radiation profile, synchronizing radiation irradiation and radiographic images, and removing noise signals in the case of treating a patient or the like by using radiation.

14 Claims, 8 Drawing Sheets

RADIATION IMAGING DEVICE AND RADIATION IMAGING SYSTEM

CROSS-REFERENCE TO RELATED APPLICATIONS

This application claims priority to and the benefit of Korean Patent Application No. 10-2023-0130475 filed in the Korean Intellectual Property Office on Sep. 27, 2023, the entire contents of which are incorporated herein by reference.

TECHNICAL FIELD

The present invention relates to a radiation imaging device and a radiation imaging system, and more particularly, to a radiation imaging device and a radiation imaging system capable of monitoring, in real time, a radiation profile, synchronizing radiation irradiation and radiographic images, and removing noise signals in the case of treating a patient or the like by using radiation.

BACKGROUND ART

Radiation therapy has often been applied to cancer patients and the like for many years. In particular, recently, proton therapy and the like have been in the limelight. The proton therapy may significantly reduce adverse effects after treatment by reducing the amount of radiation emitted to normal tissue other than tumor sites in comparison with X-ray therapy used in the related art.

However, the proton therapy device in the related art has difficulty in monitoring, in real time, a proton profile and energy transferred to protons in the case of irradiating an actual patient with the protons. Therefore, the proton therapy device in the related art is set to irradiate a predetermined position with a predetermined amount of energy and then irradiates a determined position on a patient with protons with a determined amount of energy. Therefore, there is no method capable of monitoring, in real time, whether an appropriate amount of energy has been transferred to an appropriate diseased part in the case of actually irradiating the patient with radiation during the proton therapy in the related art.

FIG. 8 is a view illustrating a configuration of a 'radiation imaging system (U.S. Pat. No. 10,690,787)' filed by the present applicant.

With reference to FIG. 8, a radiation imaging system 1200 may include a radiation-emission device 1205 and a radiation imaging device 1206, and the radiation imaging device 1206 may include a top electrode 1210, an electrical insulation layer 1220, and a charge collection electrode 1230. The radiation imaging device 1206 further includes a charge-integrating amplifier 1240, a transistor 1250, and a storage capacitor 1260.

Prior to radiation beam exposure, a bias voltage is applied to the top electrode 1210, and a gate-off voltage is applied to all gate electrodes of a pixel thin film transistor (TFT). At a time point at which charged particles traverse the electrical insulation layer 1220, continuous ionization along a path for the charged particles may form a conductive channel that allows an electric current to be conducted from the top electrode 1210 to the collection electrode 1230. Meanwhile, during the radiation beam exposure, the ionization channel current of the electrical insulation layer 1220 increases in proportion to intensity or dose of radiation, and charges of a local ionization channel on each pixel are stored in the storage capacitor 1260. The charge signal may pass through the amplifier 1240, and the charge signal may be digitized by a processing computer or the like and processed into an image.

In this case, in case that the radiation imaging system 1200 having the above-mentioned configuration is used, it is essential to synchronize the radiation imaging device 1206 and the radiation-emission device 1205 that emits radiation. Because the radiation imaging system 1200 has difficulty in synchronization, there is a burden to make a video with a frame rate of at least twice a frequency of the emitted radiation.

In addition, in case that images are captured by using the radiation imaging device 1206, a so-called lag phenomenon may occur in which an afterimage remains on a previous image, and the lag phenomenon may hinder the real-time monitoring.

Further, in case that the above-mentioned radiation imaging system 1200 is used, it is difficult to monitor, in real time, energy of radiation emitted to an object, such as a patient, by the radiation-emission device 1205.

In addition, in the above-mentioned radiation imaging system 1200, the top electrode 1210 has a structure exposed directly to the atmosphere, i.e., the air. In this case, in case that the top electrode 1210 is irradiated with radiation, the air adjacent to the top electrode 1210 may be ionized, which may cause a noise signal.

SUMMARY OF THE INVENTION

The present invention has been made in an effort to solve the above-mentioned problem, and an object of the present invention is to provide a radiation imaging device and a radiation imaging system capable of monitoring, in real time, a radiation profile in the case of treating a patient by emitting radiation.

The present invention has also been made in an effort to provide a radiation imaging device and a radiation imaging system capable of synchronizing a radiation-emission device and the radiation imaging device when radiation is emitted, creating a lag parameter that may prevent a lag phenomenon of an image, and measuring, in real time, a cumulative amount of energy transferred to a patient or the like by radiation.

The present invention has also been made in an effort to provide a radiation imaging device and a radiation imaging system capable of reducing a noise signal by preventing a top electrode of the radiation imaging device from being exposed directly to the air.

The objects of the present invention may be achieved by a radiation imaging device including: a first electrode unit configured to receive a voltage and generate a charge signal when the first electrode unit is irradiated with radiation; a plurality of pixel units provided below the first electrode unit and configured to collect and transmit the charge signal; a signal processing unit connected to the first electrode unit and configured to acquire and analyze an electric current signal generated by the first electrode unit; and an image processing device configured to create an image on the basis of the charge signal transmitted from the plurality of pixel units and a signal transmitted from the signal processing unit.

In this case, the first electrode unit may include: a first electrical insulation layer configured to generate the charge signal by being ionized when the first electrical insulation layer is irradiated with the radiation; and a first top electrode provided on a top surface of the first electrical insulation layer and configured to receive a voltage.

Further, the signal processing unit may include: a signal converter connected to the first top electrode and configured to acquire the electric current signal and convert the electric current signal into a voltage signal; and a signal analyzer configured to analyze a waveform of the voltage signal.

Meanwhile, the signal analyzer may include at least one of: an initial signal generator configured to generate an initiation signal by analyzing the waveform of the voltage signal so that an image processing process on the charge signal transmitted from the plurality of pixel units is initiated in the image processing device; a parameter creator configured to create a lag parameter required for image processing by analyzing the waveform of the voltage signal and transmit the lag parameter to the image processing device; and an energy measurer configured to measure energy of the radiation by analyzing the waveform of the voltage signal.

In one embodiment, the initial signal generator may generate the initiation signal at a time point at which a value of the voltage signal reaches a threshold voltage value.

In addition, the parameter creator may create the lag parameter with respect to continuous first and second voltage signals by using a relationship between a peak voltage of the first voltage signal and difference in values between a basal level of the first voltage signal and a basal level of the second voltage signal.

In addition, the image processing device may perform a process of correcting a created image related to the second voltage signal by using the lag parameter.

Meanwhile, the pixel unit may include: a bottom electrode configured to collect the charge signal; a storage capacitor connected to the bottom electrode and configured to store the charge signal; and a transistor.

Meanwhile, the objects of the present invention may be achieved by a radiation imaging device including: a first electrode unit configured to receive a voltage and generate a charge signal when the first electrode unit is irradiated with radiation; a second electrode unit provided above the first electrode unit and configured to prevent a top surface of the first electrode unit from coming into contact with air; a plurality of pixel units connected to a bottom portion of the first electrode unit and configured to collect and transmit the charge signal; a signal processing unit connected to the second electrode unit and acquire and analyze an electric current signal generated by the second electrode unit; and an image processing device configured to create an image on the basis of the charge signal transmitted from the plurality of pixel units and a signal transmitted from the signal processing unit.

In this case, the first electrode unit may include: a first electrical insulation layer configured to generate the charge signal by being ionized when the first electrical insulation layer is irradiated with the radiation; and a first top electrode provided on a top surface of the first electrical insulation layer and configured to receive a voltage, and the second electrode unit may include: a second electrical insulation layer provided on the top surface of the first top electrode and configured to prevent the first top electrode from coming into contact with air and generate the charge signal by being ionized when the second electrical insulation layer is irradiated with the radiation; and a second top electrode provided on a top surface of the second electrical insulation layer and configured to be irradiated with the radiation.

Meanwhile, the signal processing unit may include: a signal converter connected to the second top electrode and configured to acquire the electric current signal and convert the electric current signal into a voltage signal; and a signal analyzer configured to analyze a waveform of the voltage signal.

In addition, the signal analyzer may include at least one of: an initial signal generator configured to generate an initiation signal by analyzing the waveform of the voltage signal so that the image processing device initiates an image processing process on the charge signal transmitted from the plurality of pixel units; a parameter creator configured to create a lag parameter required for image processing by analyzing the waveform of the voltage signal and transmit the lag parameter to the image processing device; and an energy measurer configured to measure energy of the radiation by analyzing the waveform of the voltage signal.

Further, the pixel unit may include: a bottom electrode configured to collect the charge signal; a storage capacitor connected to the bottom electrode and configured to store the charge signal; and a transistor.

In addition, the objects of the present invention may be achieved by a radiation imaging system including: a radiation irradiation device configured to emit radiation; and a radiation imaging device configured to transmit the radiation emitted from the radiation irradiation device and create an image in response to the radiation, in which the radiation imaging device includes: a first electrode unit configured to receive a voltage and generate a charge signal when the first electrode unit is irradiated with the radiation; a second electrode unit provided above the first electrode unit and configured to prevent a top surface of the first electrode unit from coming into contact with air; a plurality of pixel units connected to a bottom portion of the first electrode unit and configured to collect and transmit the charge signal; a signal processing unit connected to the second electrode unit and configured to acquire and analyze an electric current signal generated by the first electrode unit; and an image processing device configured to create an image on the basis of the charge signal transmitted from the plurality of pixel units and a signal transmitted from the signal processing unit.

In this case, the radiation irradiation device may be configured as a proton beam emitter.

In addition, the radiation imaging device may be disposed between the proton beam emitter and an object so that the object is irradiated with a proton beam after the proton beam emitted from the proton beam emitter passes through the radiation imaging device.

According to the present invention, it is possible to monitor, in real time, the radiation profile in the case of treating a patient or the like by emitting radiation.

In addition, according to the present invention, it is possible to synchronize the radiation-emission device and the radiation imaging device in the case of emitting radiation, create the lag parameter that may prevent the lag phenomenon of the image, and measure, in real time, a cumulative amount of energy transferred to a patient or the like by radiation.

Further, according to the present invention, it is possible to reduce a noise signal by preventing the top electrode of the radiation imaging device from being exposed directly to the air.

The foregoing summary is illustrative only and is not intended to be in any way limiting. In addition to the illustrative aspects, embodiments, and features described above, further aspects, embodiments, and features will become apparent by reference to the drawings and the following detailed description.

Figure 1:
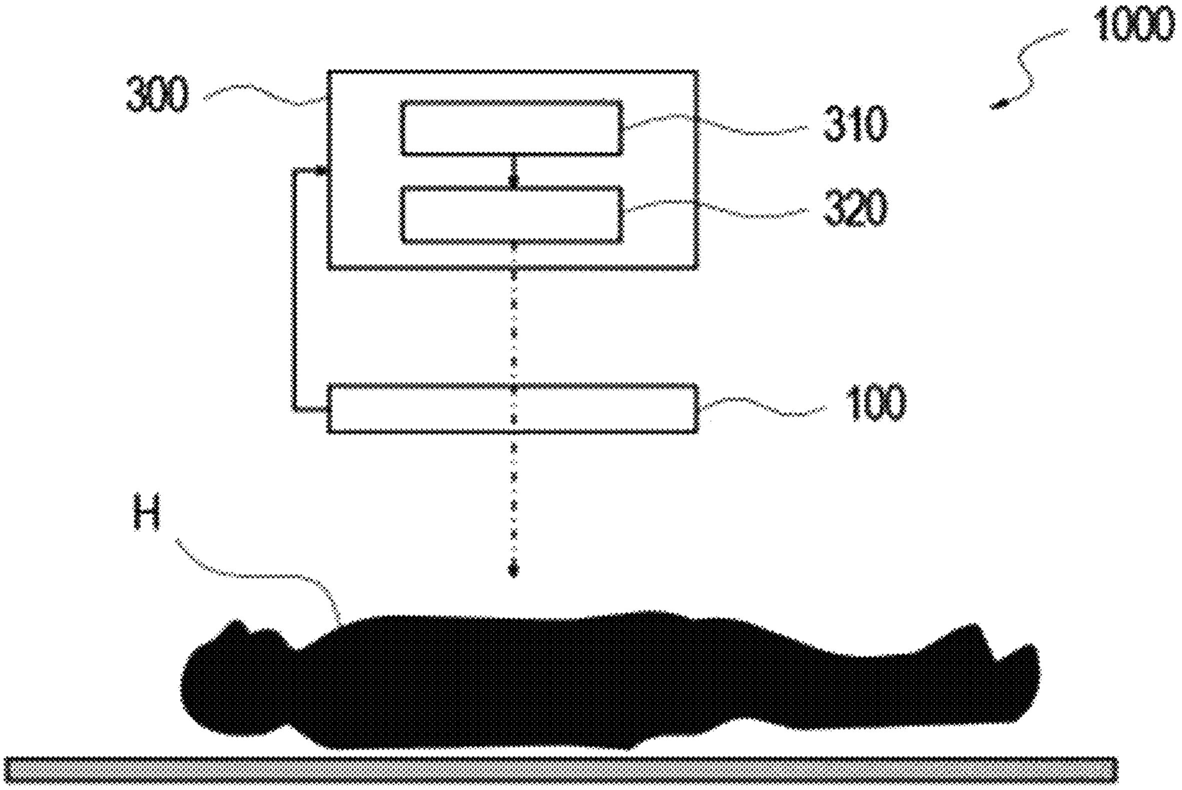
FIG. 1 is a schematic view illustrating a configuration of a radiation imaging system according to an embodiment of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter, structures of a radiation imaging device and a radiation imaging system according to an embodiment of the present invention will be described in detail with reference to the drawings.

FIG. 1 is a schematic view illustrating a configuration of a radiation imaging system 1000 according to the embodiment of the present invention.

With reference to FIG. 1, the radiation imaging system 1000 may include a radiation irradiation device 300 configured to emit radiation, and a radiation imaging device 100 configured to transmit the radiation emitted from the radiation irradiation device 300 and create an image in response to the radiation.

Radiation therapy has often been applied to cancer patients and the like for many years. In particular, recently, proton therapy and the like have been in the limelight. The proton therapy may significantly reduce adverse effects after treatment by reducing the amount of radiation emitted to normal tissue other than tumor sites in comparison with X-ray therapy used in the related art.

However, the proton therapy device in the related art has difficulty in monitoring, in real time, a proton profile and energy transferred to protons in the case of irradiating an actual patient with the protons. Therefore, the proton therapy device in the related art is set to irradiate a predetermined position with a predetermined amount of energy and then irradiates a patient with protons in a determined way. Therefore, there is no method capable of monitoring, in real time, whether an appropriate amount of energy has been transferred to an appropriate diseased part in the case of actually irradiating the patient with radiation during the proton therapy in the related art.

The radiation imaging system 1000 according to the present invention has been devised to solve the above-mentioned problem, and the radiation imaging system 1000 may be used for an apparatus for treating patients by emitting radiation, such as proton beams, to objects such as the patients.

The radiation irradiation device 300 may emit charged particle radiation, and the charged particle radiation may include ion beam radiation. Examples of the charged particle radiation or the ion beam radiation may include proton beams, helium ion beams, carbon ion beams, heavy ion beams, electron beams, muon beams, pion beams, and the like. The present invention will be described on the premise that the radiation irradiation device 300 is configured as a proton beam emitter.

The radiation irradiation device 300 may include a proton accelerator 310 and a proton shaper 320.

The emitted proton particle may be accelerated by the proton accelerator 310. The proton particle accelerated by the proton accelerator 310 passes through the proton shaper 320 to form a beam with a desired shape.

For example, in the case of treating a tumor of a patient H, the proton shaper 320 may shape the proton beam accelerated from the proton accelerator 310 so that the proton beam has a diameter corresponding to a diameter of the tumor (or a size predetermined depending on the tumor). The proton shaper 320 may include a magnet, a coil, a collimator, and the like and shape the accelerated proton beam.

The radiation imaging device 100 may be disposed between the radiation irradiation device 300 and the object so that the object is irradiated with the proton beam after the proton beam emitted from the radiation irradiation device 300 passes through the radiation imaging device 100.

In case that the object is irradiated with radiation, the radiation imaging system 1000 may monitor, in real time, a position irradiated with the radiation and energy transferred by the radiation.

Figure 2:
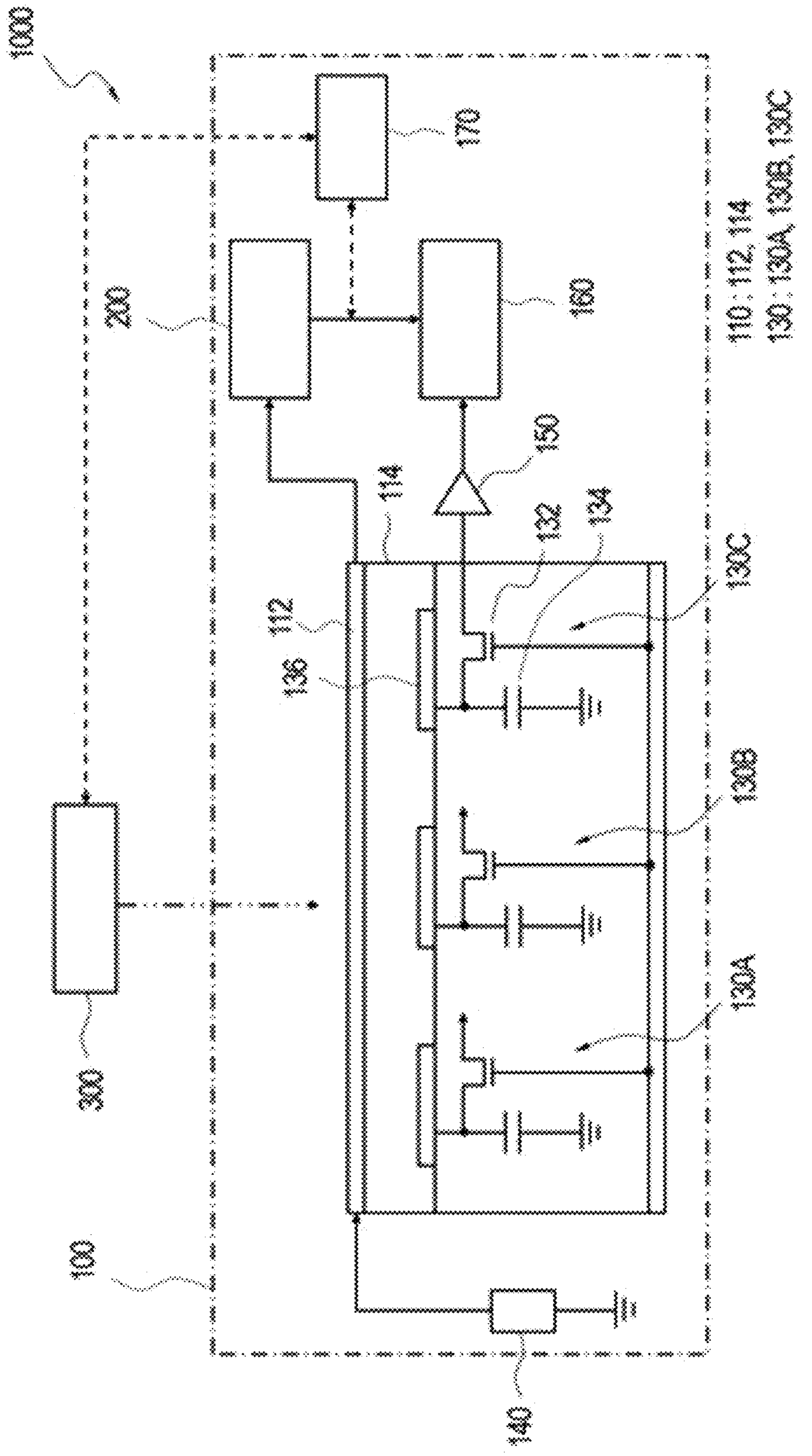
FIG. 2 is a view illustrating a configuration of a radiation imaging device of the radiation imaging system.

FIG. 2 is a view illustrating a configuration of the radiation imaging device 100 in the radiation imaging system 1000.

For reference, U.S. Pat. No. 10,690,787 may be integrated with the present specification to describe the present invention.

With reference to FIG. 2, the radiation imaging device 100 may include a first electrode unit 110 configured to receive a voltage and generate a charge signal when the first electrode unit 110 is irradiated with radiation, a plurality of pixel units 130 connected to a bottom portion of the first electrode unit 110 and configured to collect and transmit the charge signals, and a signal processing unit 200 connected to the first electrode unit 110 and configured to acquire and process an electric current signal generated by the first electrode unit 110.

In addition, the radiation imaging device 100 may further include an image processing device 160 configured to create images in response to the charge signals transmitted from the plurality of pixel units 130 and the signal transmitted from the signal processing unit 200.

In this case, the first electrode unit 110 may include a first electrical insulation layer 114 configured to generate the charge signal by being ionized when the first electrical insulation layer 114 is irradiated with radiation, and a first top electrode 112 provided on a top surface of the first electrical insulation layer 114 and configured to receive a voltage.

The first electrical insulation layer 114 may include organic compounds, such as polytetrafluoroethylene (TEFLON) and acrylic resin, including low Z materials (e.g., chemical elements having a low atomic number of protons in nuclei), such as hydrogen (H), oxygen (O), carbon (C), nitrogen (N), and fluorine (F). For example, the first electrical insulation layer 114 may be made of parylene, benzocyclobutene (BCB), polyimide film (KAPTON), or the like with high dielectric strength. However, the present invention is not limited thereto.

Meanwhile, the first electrical insulation layer 114 may be configured by depositing a parylene or polyimide film. In particular, bonding may be used for any one of the parylene and polyimide films (KAPTON) by preparing a film tape with a thickness of 50 microns.

The first top electrode 112 is provided on the top surface of the first electrical insulation layer 114. The first top electrode 112 may be formed by sputtering deposition, vacuum deposition (thermal evaporation), and/or bonding and made of any conductive material such as metal. A voltage may be applied to the first top electrode 112 by a power supply unit 140.

Meanwhile, the pixel unit 130 may include a bottom electrode 136 configured to collect the charge signal, a capacitor 134 connected to the bottom electrode 136 and configured to store the charge signal, a transistor 132.

The bottom electrode 136 may be provided on a bottom surface of the first electrical insulation layer 114 or positioned inside the bottom surface of the first electrical insulation layer 114. That is, the first top electrode 112 and the bottom electrode 136 may be respectively disposed on the opposing surfaces of the first electrical insulation layer 114 based on the first electrical insulation layer 114. For example, in case that the first top electrode 112 is disposed on the top surface of the first electrical insulation layer 114, the bottom electrode 136 may be disposed on the bottom surface of the first electrical insulation layer 114.

The bottom electrode 136 may be integrated in the first electrical insulation layer 114 and embedded in the bottom surface of the first electrical insulation layer 114. The structure may be obtained by depositing the first electrical insulation layer 114 onto a top surface of the bottom electrode 136.

In the embodiment of the present invention, the bottom electrode 136 is in direct contact with the first electrical insulation layer 114. Alternatively, an optically conductive layer is not formed between the bottom electrode 136 and the first electrical insulation layer 114. In the embodiment, the first top electrode 112 is formed directly on the top surface of the first electrical insulation layer 114 and provided to be in direct contact with the top surface of the first electrical insulation layer 114.

The pixel units 130 may be electrically connected to the first electrical insulation layer 114. At least one of the transistors 132 may be connected to each of the pixel units 130A, 130B, and 130C so that the pixel units 130 are disposed on the bottom surface of the first electrical insulation layer 114. Each of the transistors 132 may be connected between any one of the plurality of bottom electrodes 136 and a charge-integrating amplifier 150.

The bottom electrode 136 collects the charge signal from the first electrical insulation layer 114. The capacitor 134 is connected to the bottom electrode 136 and stores the charge signals collected by the bottom electrode 136. The transistor 132 may be connected to the bottom electrode 136 and serve as a switch between the capacitor 134 and the external charge-integrating amplifier 150.

Meanwhile, in case that the charged particle traverses the first electrical insulation layer 114, the first electrical insulation layer 114 is continuously ionized along a path for the charged particle, and a conductive channel is formed to allow the electric current to be conducted from the first top electrode 112 to the bottom electrode 136 of the pixel unit 130. The conductive channel is opened only when the charged particle traverses the first electrical insulation layer 114.

In addition, the conductive channel (or the ionization channel) allows the electric current to flow between the first top electrode 112 and the bottom electrode 136 having charges accumulating in the storage capacitor 134 of the pixel unit 130. The ionization channel is closed when the charged particle having energy departs from the first electrical insulation layer 114. The ionization of the first electrical insulation layer 114 may be generated by various types of charged particle beam radiation including electron beams, proton beams, helium ion beams, carbon ion beams, heavy ion beams, muon beams, pion beams, and the like. Therefore, the radiation imaging system 1000 according to the present invention may obtain images from particle radiation beams.

Meanwhile, the radiation imaging system 1000 may be configured as a proton beam system, and an image may be created by irradiating the first top electrode 112 of the radiation imaging device 100 with the proton beam. In this case, the first electrical insulation layer 114 may have a small thickness so that the proton beam may be transmitted to the patient after the proton beam generates charges on the first electrical insulation layer 114 and passes through the first electrical insulation layer 114.

For example, the first electrical insulation layer 114 may have a thickness of about 0.1 micrometers (μm) or more. However, the thickness of the first electrical insulation layer 114 is merely provided to describe an example and may be appropriately modified and selected. For example, according to another embodiment, the first electrical insulation layer 114 may have a thickness of about 10 mm or less.

Figure 3:
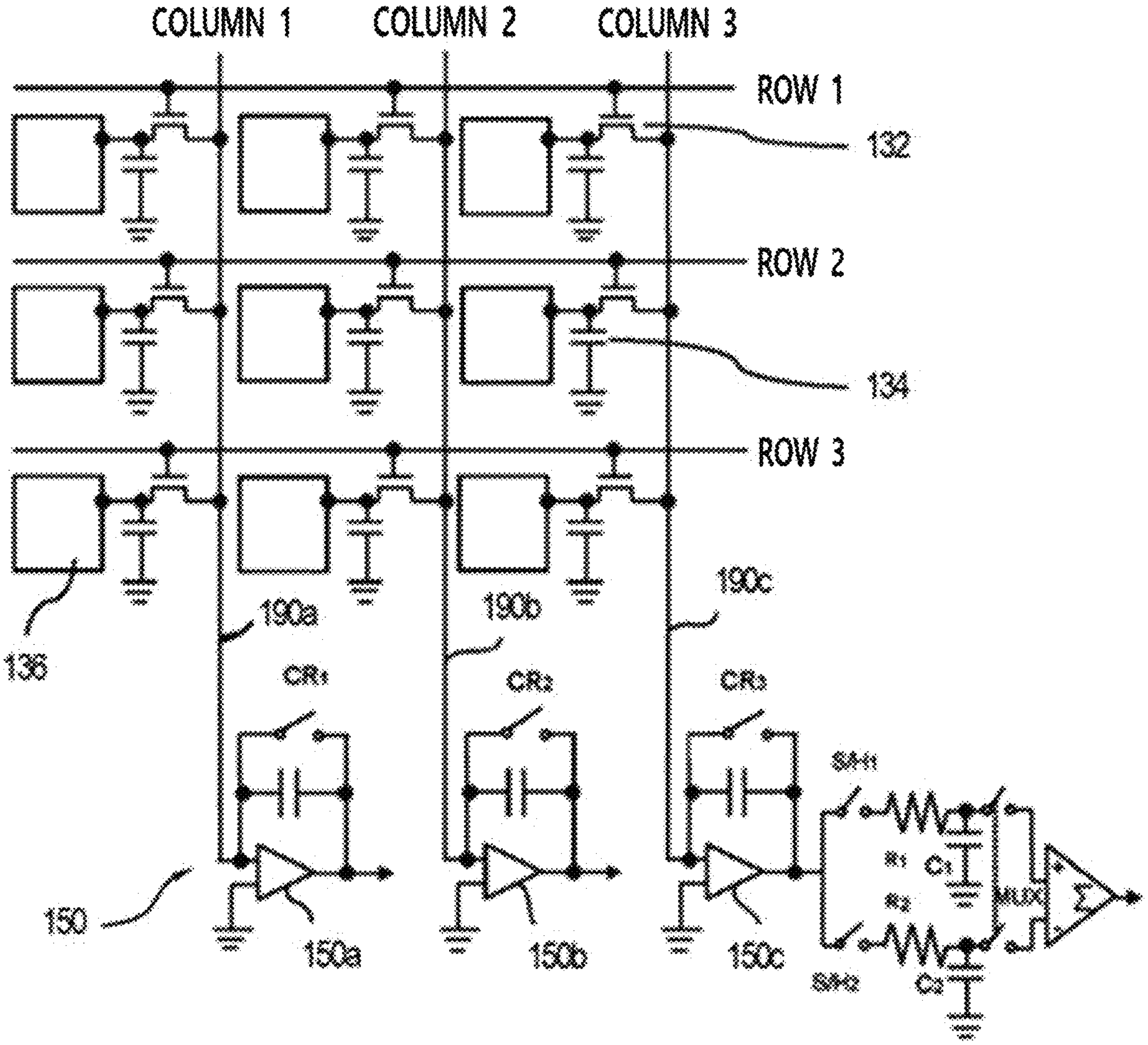
FIG. 3 is a view specifically illustrating a readout unit configured to transmit a signal from a first electrode unit to an image processing device.

Meanwhile, FIG. 3 is a view specifically illustrating a readout unit configured to transmit a signal from the first electrode unit 110 to the image processing device 160.

With reference to FIG. 3, the pixel matrices may be arranged in multiple rows and multiple columns such as N rows×M columns. FIG. 3 illustrates the arrangement of 3 rows×3 columns, but this arrangement is just an example. Other numbers of rows and other numbers of columns may be used.

In FIG. 3, gate lines of the transistors 132 in the rows may be respectively connected to a plurality of external gate drivers. Data lines of the transistors 132 in the columns orthogonal to the gate lines are respectively connected to the plurality of charge-integrating amplifiers. Prior to the radiation beam exposure, a bias voltage with a magnitude, which does not exceed a breakdown voltage of the first electrical insulation layer 114, is applied to the first top electrode 112, and a gate-off voltage is applied to all gate electrodes of the transistor 132. During the radiation beam exposure, the ionization channel current of the first electrical insulation layer 114 increases in proportion to intensity or dose of radiation, and charges of the local ionization channel of the pixel unit 130 are stored in the capacitor 134.

During the readout of the image resulting from the radiation beam exposure, the gate voltage in one row (Row 1, Row 2, or Row 3) is converted into a gate-on voltage from a gate-off voltage, such that the charge stored in the pixel unit 130 in the row passes through orthogonal data lines 190*a*, 190*b*, and 190*c* and is transmitted to charge-integrating amplifiers 150*a*, 150*b*, and 150*c*, and then the charge is digitized by the image processing device 160. After the data of one row of the matrix illustrated in FIG. 3 are completed, the potential of the gate line of the row returns to the gate-off voltage, and the transistor 132 returns to an "off" state. The potential of the next row of the gate lines is converted into the gate-on voltage from the gate-off voltage, and the stored charge flows to the orthogonal charge-integrating amplifier 150. This process may be alternately repeated until all the charges in the pixel matrix are read out.

Figure 8:
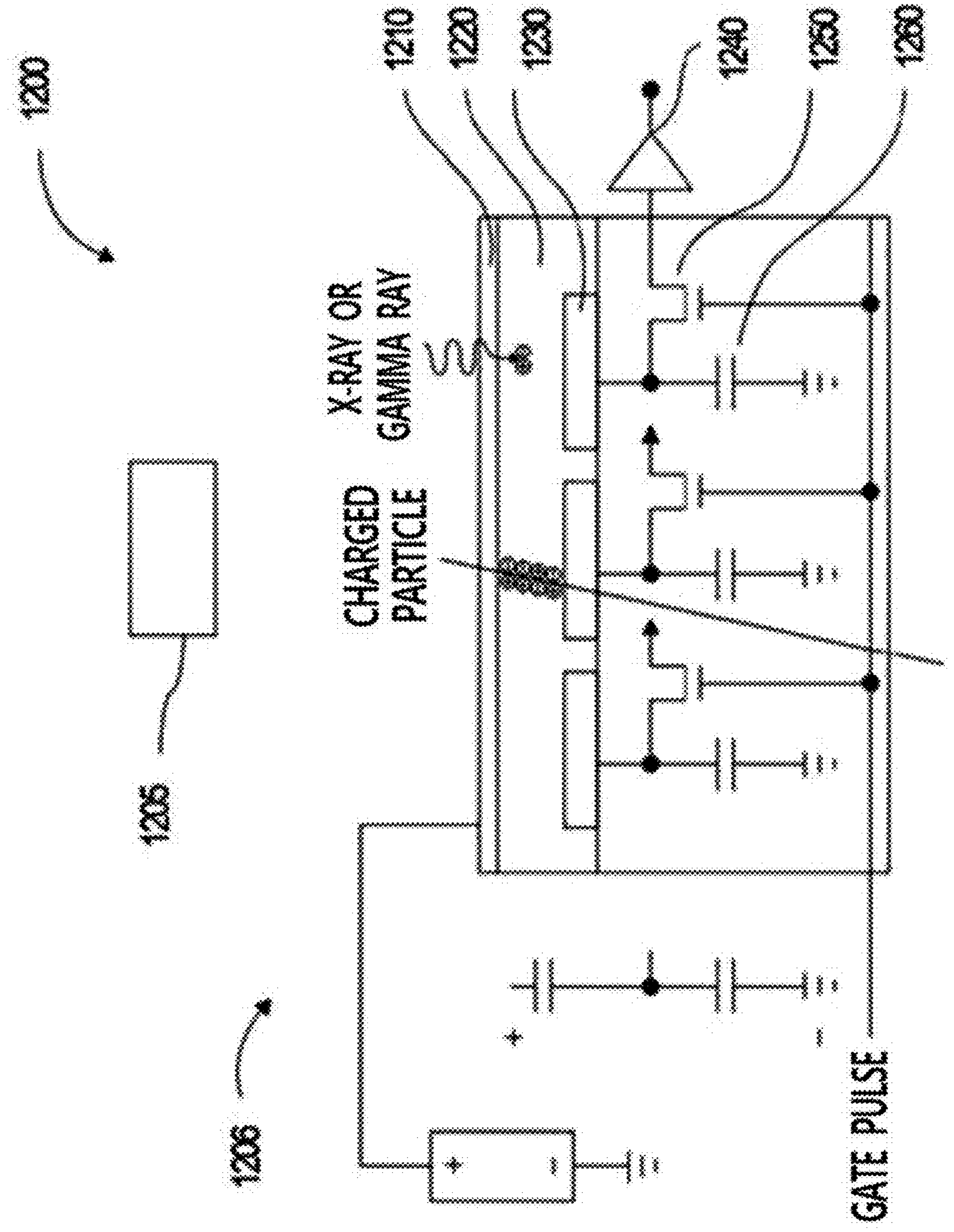
FIG. 8 Prior Art
FIG. 8 is a view illustrating a radiation imaging system in the related art.

Meanwhile, in case that the above-mentioned radiation imaging system 1200 (see FIG. 8) in the related art is used, it is necessary to synchronize the radiation imaging device 1206 and the radiation-emission device 1205 that emits the proton beam. Because the radiation imaging device 1206 in the related art has difficulty in synchronization, there is a burden to make a video with a frame rate of at least twice a frequency of the emitted radiation.

In addition, in case that images are captured by using the radiation imaging device 1206 in the related art, a so-called lag phenomenon may occur in which an afterimage remains on a previous image, and the lag phenomenon may hinder the real-time monitoring.

Further, in case that the radiation imaging system 1200 in the related art is used, it is difficult to monitor, in real time, energy of radiation emitted to an object, such as a patient, by the radiation-emission device 1205.

The radiation imaging device 100 according to the present invention may have the signal processing unit 200 to solve the above-mentioned problem.

The signal processing unit 200 may be connected to the first electrode unit 110, obtain an electric current signal generated by the first electrode unit 110, convert the electric current signal into a voltage signal, and analyze a waveform, thereby solving the above-mentioned problem.

Figure 4:
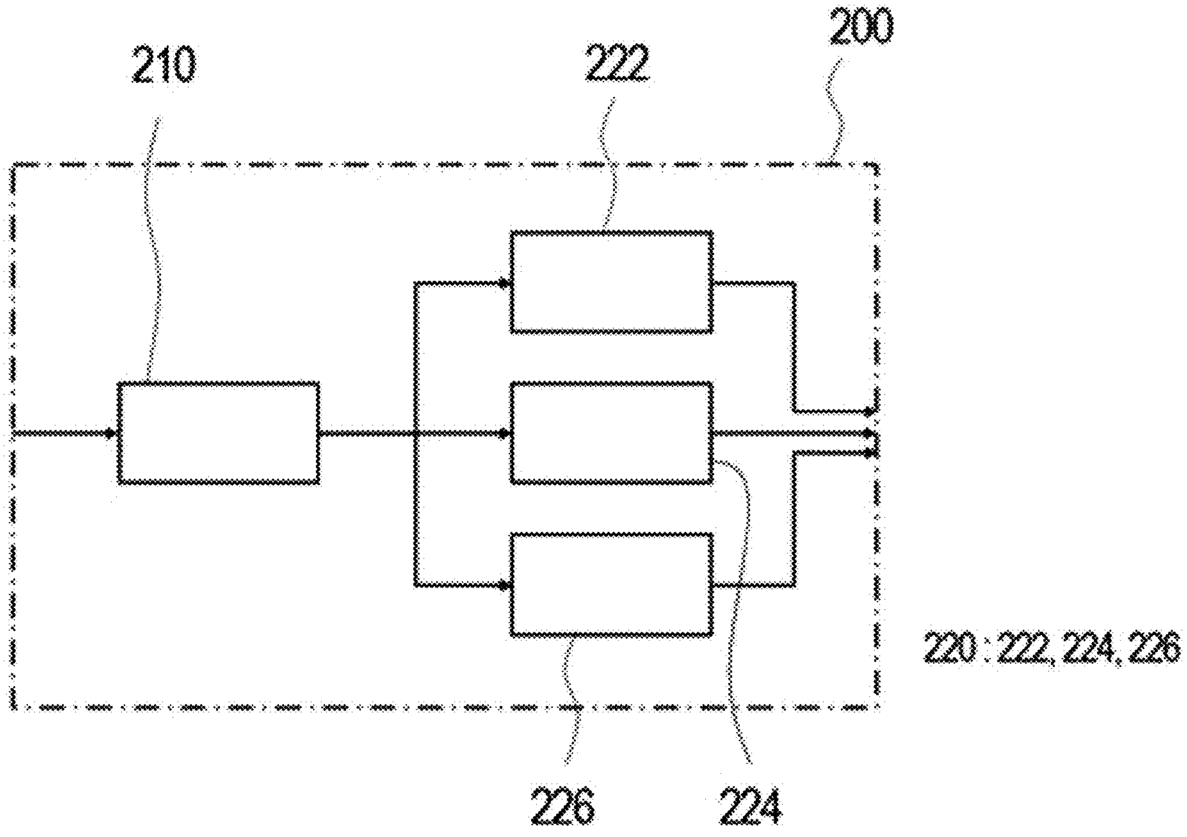
FIG. 4 is a block diagram illustrating a configuration of a signal processing unit applied to the radiation imaging system in FIG. 2.

FIG. 4 is a block diagram illustrating a configuration of the signal processing unit 200 applied to the radiation imaging system 1000 in FIG. 2.

With reference to FIG. 4, the signal processing unit 200 may include a signal converter 210 connected to the first top electrode 112 and configured to acquire an electric current signal of the first top electrode 112 and convert the electric current signal into a voltage signal, and a signal analyzer 220 configured to analyze a waveform of the voltage signal.

The signal converter 210 is connected to the first top electrode 112, acquires an electrical signal, e.g., an electric current signal from the first top electrode 112, and converts the electrical signal into a voltage signal.

As described above, the converted voltage signal is transmitted to the signal analyzer 220, such that a waveform is analyzed.

For example, the signal analyzer 220 may include at least one of an initial signal generator 222 configured to analyze the waveform of the voltage signal and generate an initiation signal for initiating an image processing process in the image processing device 160 by the charge signals transmitted from the plurality of pixel units 130, a parameter creator 224 configured to analyze the waveform of the voltage signal, create a lag parameter required for the image processing, and transmit the lag parameter to the image processing device 160, and an energy measurer 226 configured to analyze the waveform of the voltage signal and measure energy of the radiation.

Figure 5:
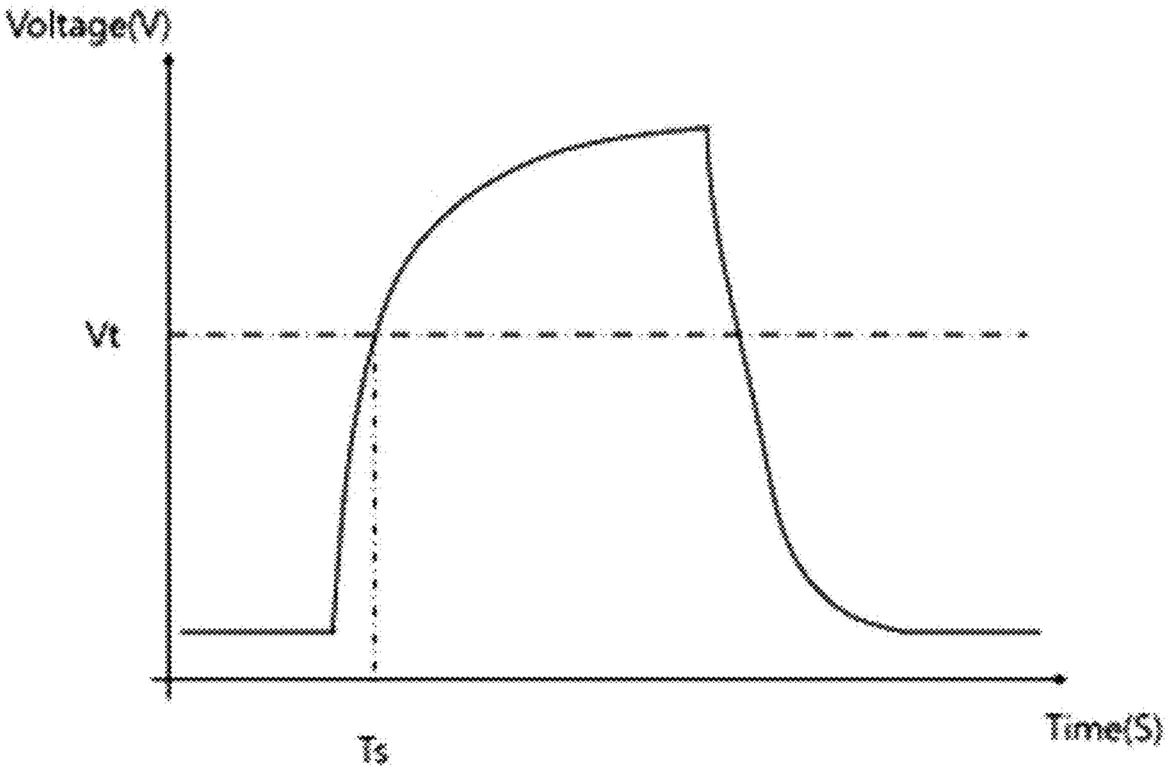
FIG. 5 is a graph illustrating a method of analyzing a waveform of a voltage signal by an initial signal generator.

FIG. 5 is a graph illustrating a method of analyzing the waveform of the voltage signal by the initial signal generator 222.

With reference to FIG. 5, the converted voltage signal has a waveform that is changed by the electric current generated by the emitted radiation. In this case, at a time point Ts at which the measured voltage signal value reaches a predetermined threshold voltage value Vt, the initial signal generator 222 may generate the initiation signal for initiating the image processing process in the image processing device 160.

The threshold voltage value Vt may be set in advance as a minimum voltage value upon which it may be determined that the radiation irradiation has occurred. In addition, the threshold voltage value may be a minimum voltage value corresponding minimum radiation irradiation for generating the charge signal in the pixel unit 130. In addition, the threshold voltage value may be determined as a minimum voltage value or the like that may allow the image processing to be performed in the image processing device 160 by the charge signal from the pixel unit 130. However, the present invention is not limited thereto, and an appropriate modification may be implemented. Meanwhile, the initiation signal may be transmitted to the image processing device 160 by a controller 170. Therefore, the radiation irradiation device 300 and the radiation imaging device 100 may be synchronized by the initiation signal.

For example, an initiation signal for initiating image acquisition may be transmitted to the image processing device 160 when it is determined that the proton beam emitted from the radiation irradiation device 300 collides with the first top electrode 112 and the voltage signal value measured by the signal processing unit 200 connected to the first top electrode 112 reaches the predetermined threshold voltage value Vt. The image processing device 160 may receive the charge signal from the pixel unit 130 and create an image in response to the transmitted signal.

The image created by the image processing device 160 may be used to determine a position irradiated with the proton beam and/or intensity or dose of the proton beam. In the embodiment, the position irradiated with the proton beam may be read out in real time from the image created by the image processing device 160. In addition, the intensity or dose of the proton beam may be determined by intensity of the image created by the image processing device 160.

Figure 6:
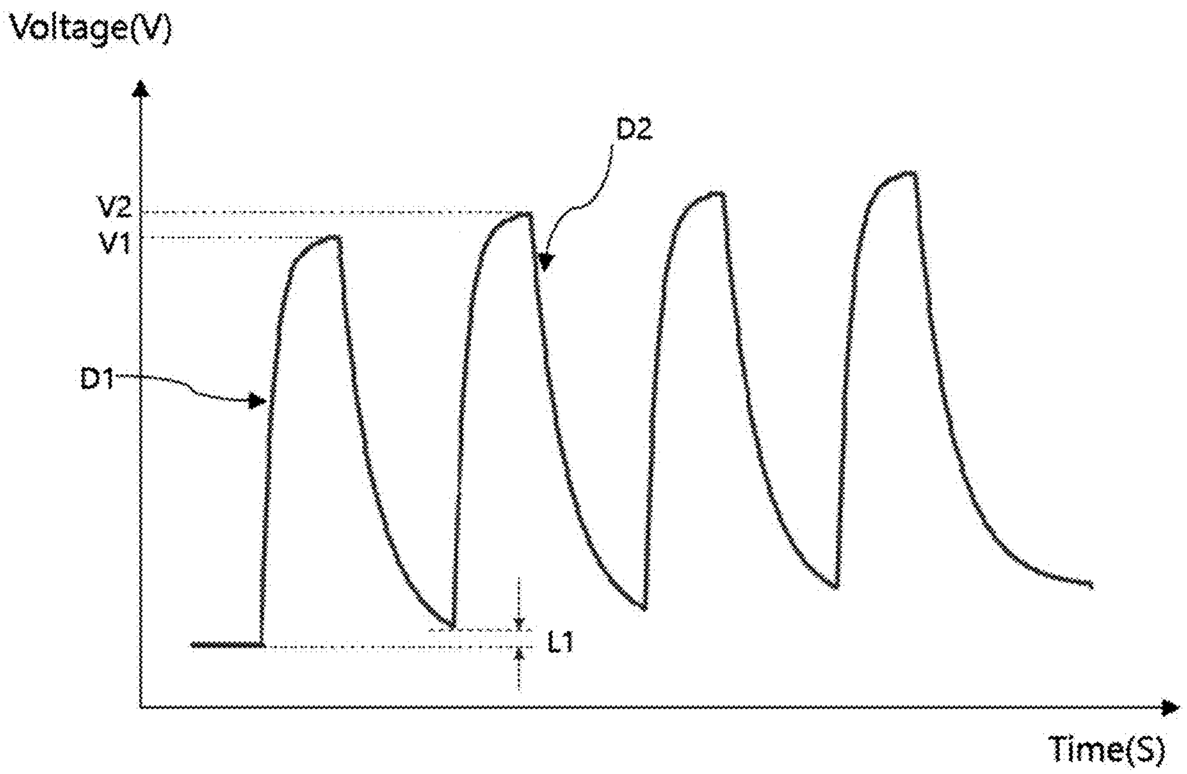
FIG. 6 is a graph illustrating a method of analyzing a waveform of a voltage signal by a parameter creator.

Meanwhile, FIG. 6 is a graph illustrating a method of analyzing the waveform of the voltage signal by the parameter creator 224.

The voltage signal converted by the signal converter 210 of the signal processing unit 200 has a waveform that is changed by the electric current generated by the emitted radiation. A so-called lag phenomenon may occur in which the electric current is collected somewhat late even when the radiation irradiation is stopped. An afterimage may remain on a previous image because of the lag phenomenon when the image is captured.

With reference to FIG. 6, the voltage signal converted by the signal converter 210 is generated by the continuous emission of the particle beam. In an example in which a first voltage signal D1 is generated by first proton beam emission and a second voltage signal D2 is generated by second proton beam emission, the first voltage signal D1 indicates a peak voltage V1, and the second voltage signal D2 indicates a peak voltage V2. However, in the case of the second voltage signal D2, a basal level of the second voltage signal D2 is different by a lag value L1 from a basal level of the first voltage signal D1 because of a lag phenomenon occurring after the first proton beam emission is ended. That is, the second voltage signal D2 is made of adding a lag voltage made by the first proton beam emission to a voltage signal made by the second proton beam emission.

The parameter creator 224 may analyze the waveform of the voltage signal and create a lag parameter LP required for the image processing in the image processing device 160. In the embodiment, the lag parameter LP may be a value made by dividing a peak voltage of a previous voltage signal by the lag value. In FIG. 6, the lag parameter LP1 for the second voltage signal D2 may be expressed by {Lag Value L1/First Peak Voltage V1}.

In case that a first image I1 is created by the first proton beam emission and a second image I2 is created by the second proton beam emission, the image processing device 160 may correct the second image I2 by using the lag parameter LP1. In the embodiment, a second image I2' with a corrected lag may be created on the basis of the equation of $I2'=I2-(I1\times LP1)$.

Therefore, it is possible to prevent an error from occurring on the image created by the image processing device 160 because of the lag phenomenon.

In the embodiment, the energy measurer 226 may analyze the waveform of the voltage signal converted by the signal converter 210 and calculate energy accumulated on the object, such as a patient, by the radiation. Therefore, the energy measurer 226 may monitor, in real time, the amount of energy accumulated on the patient by the radiation. In this case, in case that the amount of accumulated energy measured by the energy measurer 226 reaches a predetermined amount of energy, the controller may stop the operation of the radiation irradiation device 300.

Alternatively, in case that the intensity, strength, and emission time of the radiation emitted by the radiation irradiation device 300 while the amount of energy is simultaneously measured by the energy measurer 226 reach the predetermined intensity, strength, and emission time, the controller may determine that the patient is sufficiently irradiated with the radiation, and the controller may stop the operation of the radiation irradiation device 300. Energy may be lost while the radiation emitted by the radiation irradiation device 300 passes through the radiation imaging device 100. However, because a low absorption rate may be maintained in the radiation imaging device 100 of the present invention, the loss of energy does not greatly affect the intensity of the radiation emitted to the actual patient.

Meanwhile, in the radiation imaging system 1000 in FIG. 2, the first top electrode 112 of the first electrode unit 110 is exposed directly to the atmosphere, i.e., the air. In this case, in case that the first top electrode 112 is irradiated with radiation, the air adjacent to the first top electrode 112 may be ionized, which may cause a noise signal.

In addition, because the signal processing unit 200 is connected directly to the first top electrode 112 to which a voltage is applied in the radiation imaging system 1000 in FIG. 2, various types of constituent elements capable of reducing an influence caused by a high voltage of the first top electrode 112 are required.

Figure 7:
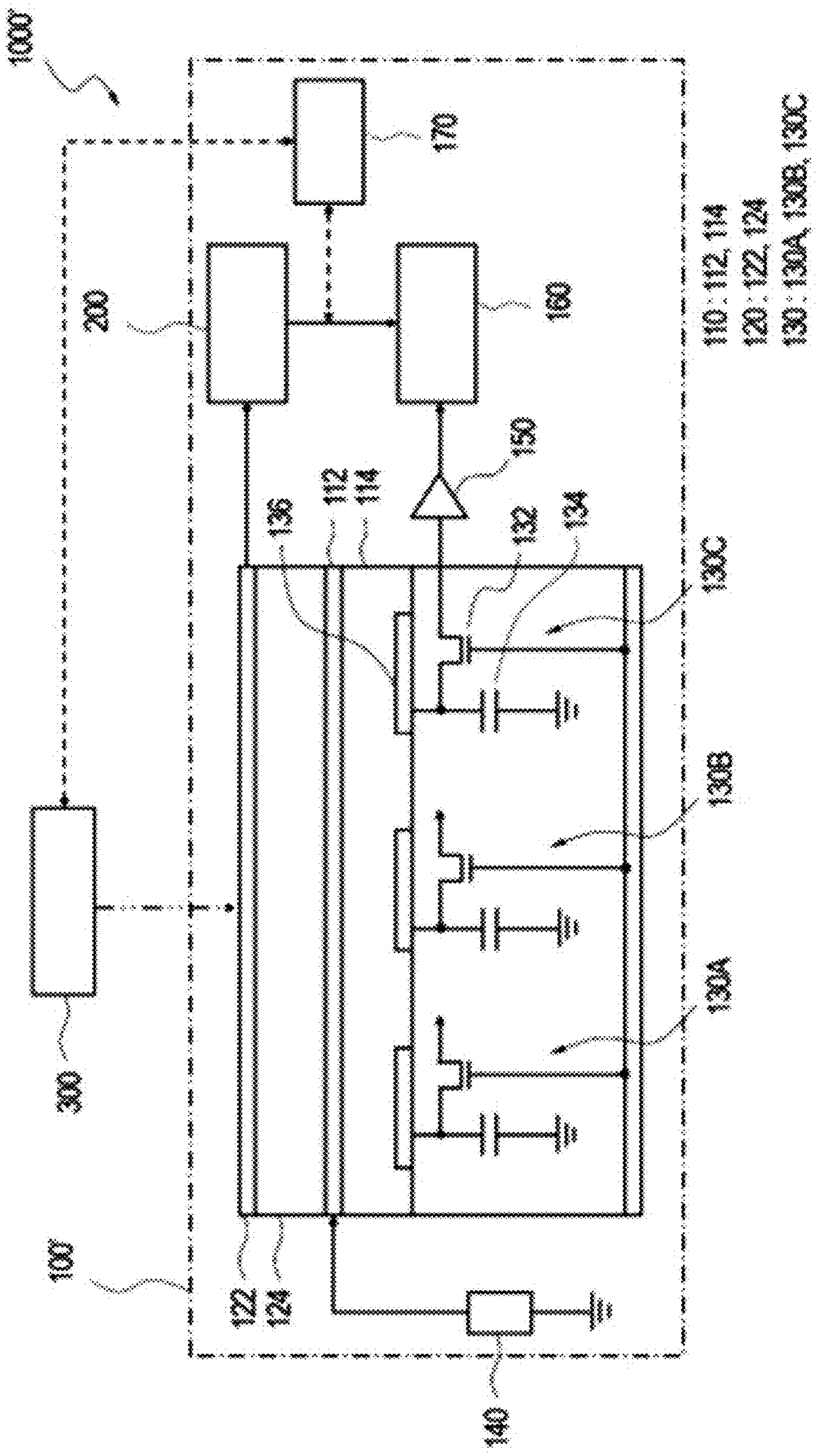
FIG. 7 is a schematic view illustrating a configuration of a radiation imaging system according to another embodiment of the present invention.

FIG. 7 illustrates a radiation imaging device 100' and a radiation imaging system 1000' according to another embodiment of the present invention.

With reference to FIG. 7, the radiation imaging device 100' may include the first electrode unit 110 configured to receive a voltage and generate a charge signal when the first electrode unit 110 is irradiated with radiation, a second electrode unit 120 provided above the first electrode unit 110 and configured to prevent the top surface of the first electrode unit 110 from coming into contact with air, the plurality of pixel units 130 connected to the bottom portion of the first electrode unit 110 and configured to collect and transmit the charge signals, and the signal processing unit 200 connected to the second electrode unit 120 and configured to acquire and analyze the electric current signal generated by the second electrode unit 120.

In addition, the radiation imaging device 100' may further include the image processing device 160 configured to create images in response to the charge signals transmitted from the plurality of pixel units 130 and the signal transmitted from the signal processing unit 200.

The radiation imaging device 100' according to the present embodiment may further include the second electrode unit 120 provided above the first electrode unit 110 and configured to prevent the first top electrode 112 of the first electrode unit 110 from being exposed directly to the air.

Specifically, the second electrode unit 120 may include a second electrical insulation layer 124 provided on the top surface of the first top electrode 112 and configured to prevent the first top electrode 112 from coming into contact with the air and generate the charge signal by being ionized when the radiation is emitted, and a second top electrode 122 provided on a top surface of the second electrical insulation layer 124 and configured to be irradiated with the radiation.

That is, the second electrical insulation layer 124 of the second electrode unit 120 is formed on the top surface of the first top electrode 112 of the first electrode unit 110 and covers the top surface of the first top electrode 112, which may prevent the top surface of the first top electrode 112 from being exposed to the air.

Therefore, in case that the first top electrode 112 receives the voltage and is irradiated with the radiation, the air adjacent to the top surface of the first top electrode 112 may be ionized and prevent the occurrence of a noise signal.

Further, in the radiation imaging device 100' according to the present embodiment, the signal processing unit 200 may be connected to the second top electrode 122 of the second electrode unit 120 instead of the first top electrode 112 to which the voltage is applied.

Therefore, because the signal processing unit 200 is connected to the second top electrode 122 instead of the first top electrode 112 to which the voltage is applied directly, various types of constituent elements capable of reducing an influence caused by a high voltage are not required.

Meanwhile, because the first top electrode 112, the second top electrode 122, the first electrical insulation layer 114, the second electrical insulation layer 124, and the signal processing unit 200 of the radiation imaging device 100' of the radiation imaging system 1000' in FIG. 7 are similar to those of the above-mentioned embodiment in FIG. 2, a repetitive description thereof will be omitted.

The embodiments of the present invention may be represented by functional block configurations and various processing steps. The function blocks may be implemented by various numbers of hardware or/and software configurations for performing particular functions. For example, the embodiment may employ integrated circuit configurations, such as memories, processing, logics, and look-up tables, that may perform various functions under the control of one or more microprocessors or other control devices. The constituent elements of the present invention may be executed as software programs or software elements. Similarly, the embodiments may be implemented in programming or scripting languages, such as C, C++, Java, assembler, and the like, including various algorithms implemented as data structures, processes, routines, or combinations of other programming configurations. The functional aspects may be implemented as algorithms executed by one or more processors. In addition, the embodiment may employ the technologies in the related art for electronic environment configuration, signal processing, and/or data processing. The terms "mechanism," "element," "means," and "component" may be used broadly and are not limited to mechanical and physical configurations. The terms may include the meaning of a series of routines of software in conjunction with a processor or the like.

The particular practices described in the embodiment are embodiments and are not intended to limit the scope of the embodiment in any way. For brevity of the specification, the description of electronic configurations, control systems, and software in the related art and other functional aspects of the systems may be omitted. In addition, line connections or connecting members between constituent elements illustrated in the drawings illustratively indicate functional connections, physical connections, and/or connections between circuits and may be represented as replaceable or additional and various functional connections, physical connections, and/or connections between circuits in an actual apparatus. In addition, a constituent element, which is not specifically mentioned together with the term such as "essentially" or "importantly", may not be a constituent element required to be necessarily applied to the present invention.

While the present invention has been described above with reference to the exemplary embodiments in the present application, the present invention may be variously modified and changed by those skilled in the art without departing from the spirit and scope of the present invention disclosed in the claims. Accordingly, when the modified embodiments basically include the components of the claims of the present invention, it should be considered that the modified embodiments belong to the technical scope of the present invention.

As described above, the exemplary embodiments have been described and illustrated in the drawings and the specification. The exemplary embodiments were chosen and described in order to explain certain principles of the invention and their practical application, to thereby enable others skilled in the art to make and utilize various exemplary embodiments of the present invention, as well as various alternatives and modifications thereof. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A radiation imaging device, comprising:

a first electrode unit configured to receive a voltage and generate a charge signal when the first electrode unit is irradiated with radiation;

a plurality of pixel units disposed below the first electrode unit and configured to collect and transmit the charge signal;

a signal processing unit connected to the first electrode unit and configured to acquire and analyze an electric current signal generated by the first electrode unit; and an image processing device configured to create an image based on the charge signal transmitted from the plurality of pixel units and a signal transmitted from the signal processing unit, wherein the signal processing unit comprises:

a signal converter connected to a first top electrode of the first electrode unit and configured to acquire the electric current signal and convert the electric current signal into a voltage signal; and a signal analyzer configured to analyze a waveform of the voltage signal.

2. The radiation imaging device of claim 1, wherein the first electrode unit further comprises a first electrical insulation layer configured to generate the charge signal by being ionized when the first electrical insulation layer is irradiated with the radiation, and wherein the first top electrode is disposed on a top surface of the first electrical insulation layer and configured to receive a voltage.

3. The radiation imaging device of claim 1, wherein the signal analyzer comprises at least one of:

an initial signal generator configured to generate an initiation signal by analyzing the waveform of the voltage signal so that an image processing process on the charge signal transmitted from the plurality of pixel units is initiated in the image processing device;

a parameter creator configured to create a lag parameter required for image processing by analyzing the waveform of the voltage signal and transmit the lag parameter to the image processing device;

an energy measurer configured to measure energy of the radiation by analyzing the waveform of the voltage signal; or a combination thereof.

4. The radiation imaging device of claim 3, wherein the initial signal generator generates the initiation signal at a time point at which a value of the voltage signal reaches a threshold voltage value.

5. The radiation imaging device of claim 3, wherein the parameter creator creates the lag parameter with respect to continuous first and second voltage signals by using a relationship between a peak voltage of the first voltage signal and difference in values between a basal level of the first voltage signal and a basal level of the second voltage signal.

6. The radiation imaging device of claim 5, wherein the image processing device performs a process of correcting a created image related to the second voltage signal by using the lag parameter.

7. The radiation imaging device of claim 1, wherein each of the plurality of pixel units comprises:

a bottom electrode configured to collect the charge signal;

a storage capacitor connected to the bottom electrode and configured to store the charge signal; and a transistor.

8. A radiation imaging device, comprising:

a first electrode unit configured to receive a voltage and generate a charge signal when the first electrode unit is irradiated with radiation;

a second electrode unit disposed above the first electrode unit and configured to prevent a top surface of the first electrode unit from coming into contact with air;

a plurality of pixel units connected to a bottom portion of the first electrode unit and configured to collect and transmit the charge signal;

a signal processing unit connected to the second electrode unit and configured to acquire and analyze an electric current signal generated by the second electrode unit; and an image processing device configured to create an image based on the charge signal transmitted from the plurality of pixel units and a signal transmitted from the signal processing unit, wherein the signal processing unit comprises:

a signal converter connected to a second top electrode of the second electrode unit and configured to acquire the electric current signal and convert the electric current signal into a voltage signal; and a signal analyzer configured to analyze a waveform of the voltage signal.

9. A radiation imaging device, comprising:

a first electrode unit configured to receive a voltage and generate a charge signal when the first electrode unit is irradiated with radiation;

a second electrode unit disposed above the first electrode unit and configured to prevent a top surface of the first electrode unit from coming into contact with air;

a plurality of pixel units connected to a bottom portion of the first electrode unit and configured to collect and transmit the charge signal;

a signal processing unit connected to the second electrode unit and configured to acquire and analyze an electric current signal generated by the second electrode unit; and an image processing device configured to create an image based on the charge signal transmitted from the plurality of pixel units and a signal transmitted from the signal processing unit, wherein the first electrode unit comprises:

a first electrical insulation layer configured to generate the charge signal by being ionized when the first electrical insulation layer is irradiated with the radiation; and a first top electrode disposed on a top surface of the first electrical insulation layer and configured to receive a voltage, and wherein the second electrode unit comprises:

a second electrical insulation layer disposed on the top surface of the first top electrode and configured to prevent the first top electrode from coming into contact with air and generate the charge signal by being ionized when the second electrical insulation layer is irradiated with the radiation; and a second top electrode disposed on a top surface of the second electrical insulation layer and configured to be irradiated with the radiation.

10. The radiation imaging device of claim 8, wherein the signal analyzer comprises at least one of:

an initial signal generator configured to generate an initiation signal by analyzing the waveform of the voltage signal so that the image processing device initiates an image processing process on the charge signal transmitted from the plurality of pixel units;

a parameter creator configured to create a lag parameter required for image processing by analyzing the waveform of the voltage signal and transmit the lag parameter to the image processing device;

an energy measurer configured to measure energy of the radiation by analyzing the waveform of the voltage signal; or a combination thereof.

11. The radiation imaging device of claim 10, wherein each of the plurality of pixel units comprises:

a bottom electrode configured to collect the charge signal;

a storage capacitor connected to the bottom electrode and configured to store the charge signal; and a transistor.

12. A radiation imaging system, comprising:

a radiation irradiation device configured to emit radiation; and a radiation imaging device configured to transmit the radiation emitted from the radiation irradiation device and create an image in response to the radiation, wherein the radiation imaging device comprises:

a first electrode unit configured to receive a voltage and generate a charge signal when the first electrode unit is irradiated with the radiation;

a second electrode unit disposed above the first electrode unit and configured to prevent a top surface of the first electrode unit from coming into contact with air;

a plurality of pixel units connected to a bottom portion of the first electrode unit and configured to collect and transmit the charge signal;

a signal processing unit connected to the second electrode unit and configured to acquire and analyze an electric current signal generated by the first electrode unit; and an image processing device configured to create an image based on the charge signal transmitted from the plurality of pixel units and a signal transmitted from the signal processing unit, wherein the signal processing unit comprises:

a signal converter connected to a second top electrode of the second electrode unit and configured to acquire the electric current signal and convert the electric current signal into a voltage signal; and a signal analyzer configured to analyze a waveform of the voltage signal.

13. The radiation imaging system of claim 12, wherein the radiation irradiation device is configured as a proton beam emitter.

14. The radiation imaging system of claim 13, wherein the radiation imaging device is disposed between the proton beam emitter and an object so that the object is irradiated with a proton beam after the proton beam emitted from the proton beam emitter passes through the radiation imaging device.

* * * * *